(12) United States Patent
Kristensen et al.

(10) Patent No.: US 10,088,428 B2
(45) Date of Patent: Oct. 2, 2018

(54) SURFACE REFRACTIVE INDEX SCANNING SYSTEM AND METHOD

(71) Applicant: Danmarks Tekniske Universitet, Lyngby (DK)

(72) Inventors: Anders Kristensen, Frederiksberg C (DK); Christoph Vannahme, Charlottenlund (DK); Martin Dufva, Hornbæk (DK)

(73) Assignee: Danmarks Tekniske Universitet, Lyngby (DK)

( * ) Notice: Subject to any disclaimer, the term of this patent is extended or adjusted under 35 U.S.C. 154(b) by 0 days.

(21) Appl. No.: 15/309,732

(22) PCT Filed: May 8, 2015

(86) PCT No.: PCT/DK2015/050121
§ 371 (c)(1),
(2) Date: Nov. 8, 2016

(87) PCT Pub. No.: WO2015/169324
PCT Pub. Date: Nov. 12, 2015

(65) Prior Publication Data
US 2017/0269002 A1    Sep. 21, 2017

(30) Foreign Application Priority Data
May 8, 2014 (EP) .................... 14167484

(51) Int. Cl.
*G01N 21/77* (2006.01)
*H01S 3/08* (2006.01)
(Continued)

(52) U.S. Cl.
CPC ........ *G01N 21/7743* (2013.01); *G01J 3/0245* (2013.01); *G01J 3/1895* (2013.01);
(Continued)

(58) Field of Classification Search
CPC .......... G01N 21/7743; G01N 21/4133; G01N 2021/7789; G01N 2021/7776;
(Continued)

(56) References Cited

U.S. PATENT DOCUMENTS

| 5,276,321 A | 1/1994 | Chang et al. |
| 8,268,637 B2 * | 9/2012 | Cunningham ..... G01N 21/7743 422/82.11 |

(Continued)

FOREIGN PATENT DOCUMENTS

EP    1862795 A1    12/2007

OTHER PUBLICATIONS

"International Application Serial No. PCT/DK2015/050121, International Preliminary Report on Patentability dated Jul. 13, 2016", 15 pgs.

(Continued)

*Primary Examiner* — Dominic J Bologna
(74) *Attorney, Agent, or Firm* — Schwegman Lundberg & Woessner, P.A.

(57) ABSTRACT

A surface refractive index acquisition system for characterization of a sample is provided. The system comprises a grating device configured to receive the sample, and first and second grating regions. First and second grating periods are selected to provide optical resonances for light respectively in first and second wavelength bands. A light source is configured to illuminate part of the first and second grating regions simultaneously. An imaging system is configured to image light from the grating device and comprises an optical element focusing light in a transverse direction and being invariant in an orthogonal transverse direction, the optical element being oriented such that the longitudinal direction of the grating device is oriented to coincide with the invariant direction of the optical element, and an imaging spec- (Continued)

trometer comprising an entrance slit having a longitudinal direction oriented to coincide with the invariant direction of the optical element.

18 Claims, 4 Drawing Sheets

(51) Int. Cl.
    *G01J 3/08* (2006.01)
    *G01J 3/18* (2006.01)
    *G01J 3/28* (2006.01)
    *G01N 21/41* (2006.01)
    *G01J 3/02* (2006.01)
    *G01J 3/06* (2006.01)

(52) U.S. Cl.
    CPC ........ G01J 3/2823 (2013.01); G01N 21/4133 (2013.01); H01S 3/08009 (2013.01); *G01J 2003/064* (2013.01); *G01N 2021/7776* (2013.01); *G01N 2021/7789* (2013.01)

(58) Field of Classification Search
    CPC ... H01S 3/08009; G01J 3/1895; G01J 3/0245; G01J 3/2823; G01J 2003/064
    See application file for complete search history.

(56) References Cited

U.S. PATENT DOCUMENTS

| | | |
|---|---|---|
| 2007/0070355 A1 | 3/2007 | Cunningham et al. |
| 2007/0265783 A1* | 11/2007 | Mound ..................... G01J 3/02 702/8 |
| 2009/0067774 A1* | 3/2009 | Magnusson ............ B82Y 20/00 385/10 |
| 2009/0079976 A1* | 3/2009 | Cunningham ........ B01L 3/5027 356/246 |
| 2010/0008826 A1 | 1/2010 | Schulz |
| 2011/0102799 A1 | 5/2011 | Matejka et al. |
| 2011/0267623 A1* | 11/2011 | Matejka ............... G01N 21/278 356/446 |

OTHER PUBLICATIONS

"International Application Serial No. PCT/DK2015/050121, International Search Report dated Jul. 13, 2015", 4 pgs.

"International Application Serial No. PCT/DK2015/050121, Written Opinion dated Jul. 13, 2015", 10 pgs.

Cunningham, Brian T., et al., "Label-Free Assays on the BIND System", *Journal of Biomolecular Screening*, 9(6), (2004), 481-490.

Ge, Chun, et al., "Distributed feedback laser biosensor incorporating a titanium dioxide nanorod surface", *Applied Physics Letters*, 96, 163702, (2010), 3 pgs.

Lu, M., et al., "Plastic distributed feedback laser biosensor", *Applied Physics Letters*, 93, 111113, (2008), 3 pgs.

Riedl, T., et al., "Tunable organic thin-film laser pumped by an inorganic violet diode laser", *Applied Physics Letters*, 88, 241116, (2006), 3 pgs.

Schneider, D., et al., "Ultrawide tuning range in doped organic solid-state lasers", *Applied Physics Letters*, 85(11), (2004), 1886-1888.

Vannahme, Christoph, et al, "Emission wavelength of multilayer distributed feedback dye lasers", *Applied Physics Letters*, 101, 151123, (2012), 4 pgs.

Vannahme, Christoph, et al., "Nanoimprinted distributed feedback lasers comprising $TiO_2$ thin films: Design guidelines for high performance sensing", *Laser & Photonics Reviews*, 7(6), (2013), 1036-1042.

\* cited by examiner

SURFACE REFRACTIVE INDEX SCANNING SYSTEM AND METHOD

This application is a U S. National Stage Filing under 35 U.S.C. 371 from International Application No. PCT/DK2015/050121, filed on May 8, 2015, and published as WO 2015/169324 A1 on Nov. 12, 2015, which claims the benefit of priority to European Patent Application No. 14167484.6, filed on May 8, 2014, each of which is hereby incorporated by reference herein in its entirety.

FIELD OF THE INVENTION

The present invention relates to optical characterization of a sample. More specifically, the invention relates to a surface refractive index scanning system.

BACKGROUND OF THE INVENTION

U.S. Pat. No. 8,268,637 B2 discloses label-free biosensors based upon distributed feedback (DFB) laser. In one configuration, the DFB laser comprises a replica-molded, one- or two-dimensional dielectric grating coated with a laser dye-doped polymer as a gain medium. The laser dye or other active material in the active layer is pumped via an external optical source. The stimulated emission wavelength of the laser dye is modulated, i.e. shifted, by the adsorption of biomolecules on the DFB laser biosensor's surface. The reference does not teach a spatially resolved measurement of the sample.

Hence, an improved surface refractive index detecting system would be advantageous, and in particular a system providing a spatially resolved measurement of the refractive index would be advantageous.

Object of the Invention

It is a further object of the present invention to provide an alternative to the prior art.

In particular, it may be seen as an object of the present invention to provide a surface refractive index scanning system that solves the above mentioned problems of the prior art with providing a 2-dimensional spatially resolved measurement.

It may be seen as a further object of the present invention to provide a surface refractive index scanning system that allows for time- and spatially resolved measurements, preferably in a non-scanning fashion.

SUMMARY OF THE INVENTION

Thus, the above-described object and several other objects are intended to be obtained in a first aspect of the invention by providing a surface refractive index scanning system for characterization of a sample. The system comprises a grating device for holding or receiving the sample, the device comprising at least a first grating region having a first grating width along a transverse direction, and a second grating region having a second grating width in the transverse direction. The first grating region and the second grating region are adjacent in the transverse direction, wherein the first grating region has a grating period $\Lambda_1$ in a longitudinal direction being orthogonal to the transverse direction, and the second grating region has a grating period $\Lambda_2$ in the longitudinal direction. A grating period spacing $\Delta\Lambda=\Lambda_1-\Lambda_2$ is chosen to be finite. Further, the first and second grating periods are chosen to provide optical resonances for light respectively in a first wavelength band and a second wavelength band, light is being emitted, transmitted, or reflected in an out-of-plane direction, wherein the first wavelength band and the second wavelength band are at least partially non-overlapping in wavelength. The system further comprises a light source for illuminating at least a part of the grating device with light at an illumination wavelength band. Additionally, the system comprises an imaging system for imaging the emitted, transmitted or reflected light from the grating device. The imaging system comprises an optical element configured for focusing light in a transverse direction and for being invariant in an orthogonal transverse direction, the optical element being oriented such that the longitudinal direction of the grating device is oriented to coincide with an invariant direction of the optical element, and an imaging spectrometer comprising an entrance slit having a longitudinal direction oriented to coincide with the invariant direction of the optical element. In this way, a spatially resolved characterization of the refractive index of a sample on a surface of the grating device may be obtained without physically scanning the grating device or the optical components, as will be described herein below. Light recorded from the grating regions will be resonant light, i.e. having a wavelength that lies within a wavelength band around a wavelength that satisfies a resonance condition in a grating region. Since the resonance condition of the grating depends on the refractive indices of high-index and low-index grating elements and refractive index of the material present on the surface, a change in refractive index on the surface is immediately apparent as a change in resonance wavelength, i.e. a wavelength shift of the resonance peak. The optical element is adjusted to focus light from the grating regions onto the entrance slit, to maximize optical coupling. The imaging spectrometer then acts to resolve and record a spectrum for each position along the entrance slit, corresponding to each position along the longitudinal direction of the grating device. Thus, the imaging spectrometer will spatially resolve spectral responses along the longitudinal direction of the grating device. The system ensures that a spectral response from the first grating region will be imaged along a detector line in the imaging spectrometer, and a spectral response from the second grating region will be imaged along the same detector line in the imaging spectrometer. Since each of the first and second grating regions are configured to give optical resonances at different wavelengths, a spectrum recorded for one position in the longitudinal direction will in general show a first resonance peak corresponding to a response from the first grating region, and a second resonance peak corresponding to the second grating region. The grating period spacing $\Delta\Lambda$ should be chosen to spectrally separate the resonance peak from the first grating region from the resonance peak from the second grating region, also accounting for the resonance wavelength shift possibly arising from the refractive index change depending on the sample. By ensuring that the first resonance peak and the second resonance peak are well-separated in wavelength, the response may thus also be spatially resolved in the transverse direction. By detecting the peak center wavelengths and monitoring for any shifts in these wavelengths, refractive index changes in the sample may be detected in a spatially resolved manner. The spatial measurement resolution of the refractive index image will be given by the number and width of the grating regions in the transverse direction.

The invention is particularly suited for fluid samples, sample solutions, or samples suspended in a fluid.

In one embodiment of the invention, the optical element is a cylindrical lens.

In an alternative embodiment of the invention, the optical element is a bended mirror.

In the context of this specification, an orientation/direction of a first device being oriented to coincide with an orientation/direction of a second device is to be understood such that the orientation/direction of the first device when imaged onto the second device by any optical elements between the first and second devices is such that the imaged orientation/direction coincide with the physical orientation/direction of the second device. Thus, e.g. a mirror folding the optical path is irrelevant in this regard.

In an embodiment of the surface refractive index scanning system, the grating device comprises multiple structured regions, including the first grating region and the second grating region, such as a number of structured regions in the range 2-100, or 10-80, or even 20-50, wherein each of the grating regions are arranged to provide optical resonances for light respectively in corresponding wavelength bands, light is being emitted, transmitted, or reflected in an out-of-plane direction, the corresponding wavelength bands being at least partially non-overlapping. In this way, the spatial measurement resolution in the transverse direction may be increased.

In an embodiment of the surface refractive index scanning system, the first structured region and/or the second structured region are configured as a second order distributed Bragg reflector (DBR) for providing the optical resonance. In an alternative embodiment, the optical resonance is provided by a photonic crystal structure.

In an alternative embodiment, the optical resonance is provided by guided mode resonance filter (GMRF).

In an alternative embodiment, the optical resonance is provided by a plasmonic structure.

In an alternative embodiment, the optical resonance is provided by a nano-hole array.

In an embodiment of the surface refractive index scanning system, the grating device comprises a light-emitting material having an emission spectrum, wherein first structured region and the second structured region are configured such that the first wavelength range and the second wavelength range at least partially fall within the emission spectrum of the light-emitting material. In this way, the grating device is an active device that may be made to lase, with lasing wavelengths being dependent on the refractive indices at the different positions of the device. This is advantageous so as to provide narrow resonance peaks and to increase the received power levels from each position.

In an embodiment of the surface refractive index scanning system, the grating period spacing $\Delta\Lambda$ between two adjacent grating regions is in the range 0.05 nm-10 nm, such as in the range 0.1 nm-5 nm, or even in the range 0.5 nm-2 nm. A grating period spacing in this region is particularly advantageous for resolving the generally narrow resonance peaks that result in the active grating device, while also ensuring reasonable spectral bandwidth-efficiency of the whole device. This is a trade-off in that the resonance peaks must be spectrally well-separated to provide the transverse spatial resolution of the sample, i.e. have a sufficiently large $\Delta\Lambda$, while the overall bandwidth of the device should be kept as small as possible, to ensure that the whole bandwidth range may be kept within the emission spectrum of the light-emitting material. Another limiting factor for the choice of grating period spacing, which also applies to passive grating devices (as further discussed below), is that the spectral resolving bandwidth of the spectrometer should encompass the resonance peaks from all grating regions, while the spectrometer wavelength resolution should be able to resolve the individual peaks sufficiently to enable calculation of the center wavelengths associated with each peak.

In an embodiment of the surface refractive index scanning system, the light-emitting material is or comprises a dye-doped material.

In an embodiment of the surface refractive index scanning system, the dye-doped material comprises a polymer.

In an embodiment of the surface refractive index scanning system, the grating device is a passive structure for reflecting or transmitting light in the wavelength ranges.

In an embodiment of the surface refractive index scanning system, the grating period spacing $\Delta\Lambda$ between two adjacent grating regions is in the range 0.5 nm-500 nm, such as about 5 nm-200 nm, or even in the range 10 nm-100 nm.

In an embodiment of the surface refractive index scanning system, the system further comprises an optical gain material and a first cavity end reflector, and wherein the grating device is arranged as a second cavity end reflector, the gain material being disposed between the first cavity end reflector and the second cavity end reflector in an external cavity laser configuration.

In an embodiment of the surface refractive index scanning system, the system is or comprises a microscope system.

According to a second aspect of the invention, the above-described object and several other objects are intended to be obtained by a method of acquiring a surface refractive index image of a sample. The method comprises providing a grating device for holding the sample. The device comprises at least a first grating region having a first grating width along a transverse direction, and a second grating region having a second grating width in the transverse direction. The first grating region and the second grating region are adjacent in the transverse direction. The first grating region has a grating period $\Lambda_1$ in a longitudinal direction, the longitudinal direction being orthogonal to the transverse direction, and the second grating region has a grating period $\Lambda_2$ in the longitudinal direction. The grating periods are selected such that a grating period spacing $\Delta\Lambda=\Lambda_1-\Lambda_2$ is finite, the first and second grating periods are furthermore chosen to provide optical resonances for light respectively in a first wavelength band and a second wavelength band. The resonant light is emitted, transmitted, or reflected in an out-of-plane direction, wherein the first wavelength band and the second wavelength band are at least partially non-overlapping in wavelength. The method further comprises positioning the sample to be characterized onto the grating device so as to come into contact with the first and/or the second grating region, and illuminating at least a part of the grating device with light at an illumination wavelength band. Additionally, the method comprises imaging the emitted, transmitted or reflected light from the grating device with an imaging system into a 2-dimensional raw image. The imaging system comprises an optical element, configured for focusing light in a first transverse direction and for being invariant in an orthogonal transverse direction, wherein the optical element is oriented such that the longitudinal direction of the grating device is oriented to coincide with an invariant direction of the optical element. The imaging system additionally comprises an imaging spectrometer that comprises an entrance slit having a longitudinal direction oriented to coincide with the invariant direction of the optical element. The imaging spectrometer further comprises a 2-dimensional image sensor, oriented along the longitudinal direction of the entrance slit. Finally, the method comprises processing the 2-dimensional raw image to obtain a 2-dimensional map of refractive index change of the sample at the grating regions, where the processing utilizes that each row of pixels in the raw image perpendicular to the longitudinal direction of the entrance slit contains spectrally resolved resonance peaks for each grating region, each resonance peak corresponding to a position along the transverse direction of the grating device, and positions in the raw image along the longitudinal direction translates directly to positions along the longitudinal direction of the grating device.

In an embodiment of the method according to the invention, the step of processing the image comprises tracking changes in spectral positions of the resonance peaks to provide a time-resolved image of refractive index changes in the sample.

In an embodiment of the method according to the invention, processing the 2-dimensional raw image comprises for each row of pixels perpendicular to the longitudinal direction of the entrance slit, detect peak positions in pixels for resonance peaks in the row associated with each grating region. Convert each peak position in pixels to a peak wavelength value of resonance. Calculate a wavelength shift for each of the peak wavelength values of resonance with regards to reference peak values corresponding to the grating device without the sample present. Finally, calculate refractive index values from the wavelength shifts.

In an embodiment of the method, finding the peak position in pixels for each of the grating region comprises finding a peak pixel as a pixel with a highest intensity reading within a range of pixels associated with that grating region. The method further comprising calculating the peak position in pixels from a range of pixels around the peak pixel using a numerical method. In the paper Vannahme, et. al, Laser Photonics Rev., 1-7 (2013), DOI 10.1002/lpor.201300083, the present inventors have in section 2.5 thereof described data processing of a single peak in spectrometer data. This paper, in particular section 2.5, is hereby incorporated by reference, for at least the purpose of two methods of finding peak wavelength positions.

In an embodiment of the method, the numerical method is a center of mass calculation.

In an embodiment of the method, the numerical method is a function fit, such as a Lorentzian fit.

In alternative embodiments of the method, pixel values are converted to wavelength values before finding the peak positions.

In one such embodiment, finding the peak wavelength position comprises finding a peak intensity wavelength value for the grating region in question, and finding the peak wavelength by a weighted fit, such as a center of mass calculation or a Lorentzian fit. Thus, this embodiment is analogous to the above-mentioned embodiment, except that calculations are performed on wavelength values, rather than pixel values.

The first and second aspects of the present invention may each be combined with any of the other aspects. These and other aspects of the invention will be apparent from and elucidated with reference to the embodiments described hereinafter.

BRIEF DESCRIPTION OF THE FIGURES

The surface refractive index scanning system according to the invention will now be described in more detail with regard to the accompanying figures. The figures show one way of implementing the present invention and is not to be construed as being limiting to other possible embodiments falling within the scope of the attached claim set.

DETAILED DESCRIPTION OF AN EMBODIMENT

Figure 1:
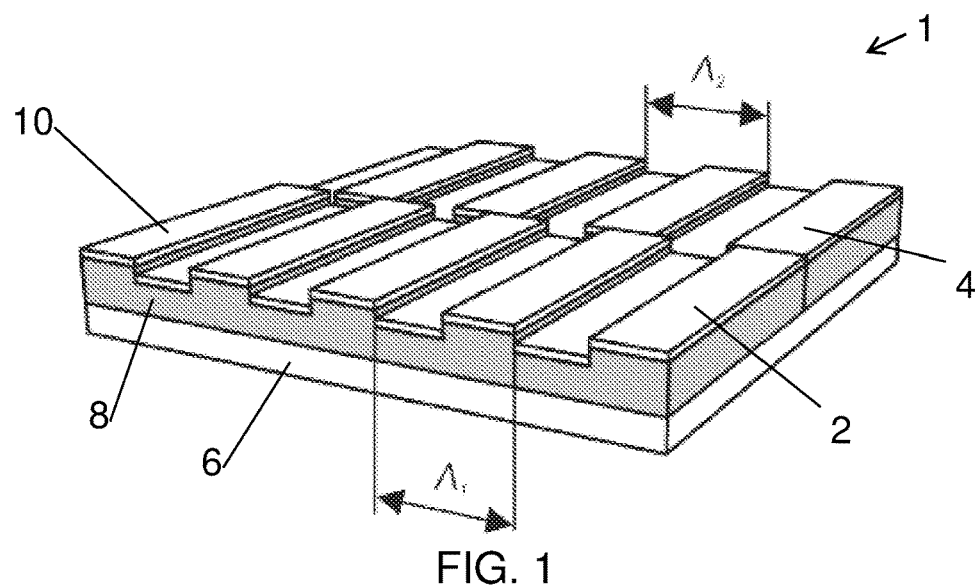
FIG. 1 illustrates a grating device as comprised by the inventive system.

FIG. 1 shows a grating device 1 as comprised by the inventive system. Here, two grating regions are illustrated, i.e. the first 2 and the second 4 region, having a grating period $\Lambda_1$ and $\Lambda_2$, respectively. The grating period spacing between the two grating regions $\Delta\Lambda$ should be chosen to spectrally separate the resonance from the first grating region from the resonance from the second grating region. Preferably the grating period should also be selected to minimize the bandwidth requirement of the whole grating device 1. In an embodiment, the grating device comprises a glass substrate 6, onto which is deposited a polymer-containing layer 8. The polymer-containing layer 8 may be doped with an active material, such as a dye for use in active embodiments of the inventive system. Alternatively, the polymer-containing layer 8 may be passive for use in passive embodiments. Finally, the grating device 1 preferably comprises a high refractive index layer, e.g. a $TiO_2$-layer or a $Ta_2O_5$-layer 10 on a top side of the device, which acts to increase an optical overlap between a resonant light field within a grating region and a fluid sample put in contact with the top side of the device.

An example of a grating device as fabricated by the inventors, was made using a 4 inch Borofloat glass wafer as substrate. The glass wafer had a thickness of 500 μm, but could in general have a thickness in the range of about 50 μm-2 mm.

An alternative embodiment could also be made in a plastic material such as COC, or in a different glass. The polymer-containing layer was formed as a dye doped thin film, or more specifically as a Pyrromethene 597 doped Ormocomp-layer, having a thickness of 400 nm. In general the polymer-containing layer could have the thickness in the range of about 200 nm-500 nm, and could also be made in other material, such as poly-methyl methacrylate (PMMA) or SU8. Finally, the example device comprised a high index layer fabricated as an ion beam evaporated $TiO_2$-layer, with a thickness of 25 nm (possible thickness range of about 0 nm-400 nm).

In the example device, 40 grating regions were made, with grating widths of 25 μm. The grating periods $\Lambda_i$ were chosen in the range $\Lambda_i$=351 nm . . . 391 nm, with a constant grating period spacing $\Delta\Lambda$=1 nm to result in resonances in the wavelength range $\lambda$~540 nm-600 nm.

In another example device, 11 grating regions were made, with grating widths of 90 μm. The grating periods $\Lambda_i$ were chosen in the range $\Lambda_i$=370 nm . . . 380 nm, with a constant grating period spacing $\Delta\Lambda$=1 nm to result in resonances in the wavelength range $\lambda$~565 nm-585 nm.

Figure 2:
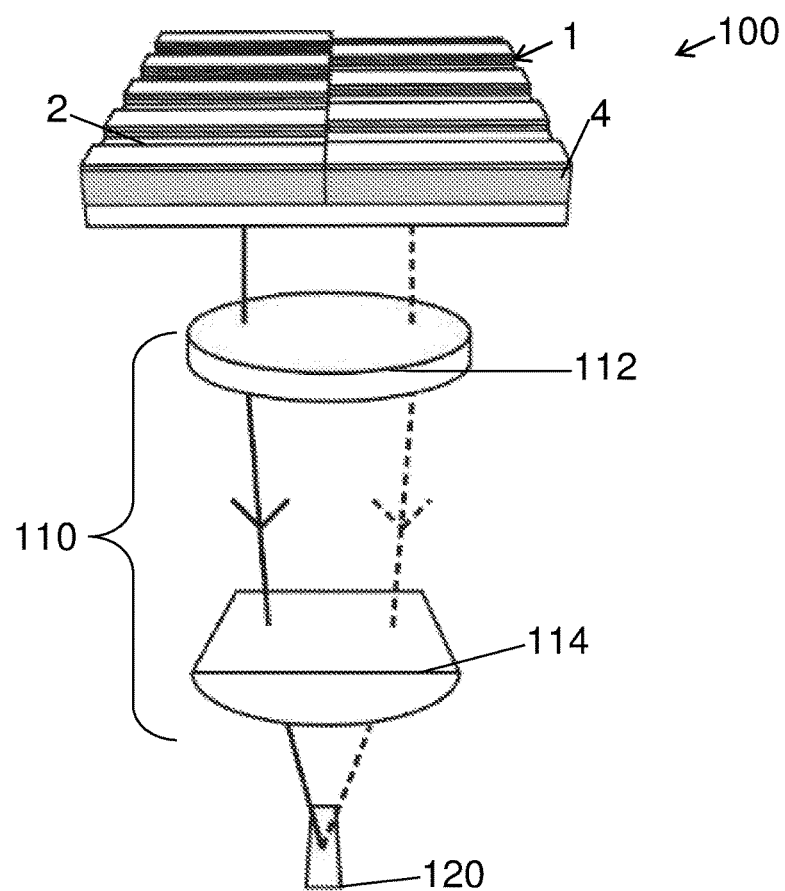
FIG. 2 illustrates a simplified setup according to the invention.

FIG. 2 schematically shows the surface refractive index scanning system 100 according to the invention. The system comprises a grating device 1, as discussed above in connection to FIG. 1. The system 100 further comprises an imaging system 110, here illustrated as a lens 112 and a cylindrical lens 114. The imaging system 110 is configured to collect light from the grating device 1 and focus it onto an entrance slit 120 on an imaging spectrometer. It is noticed that the first grating region 2 and the second grating region 4 are imaged onto the same elongated line and onto the entrance slit 120 for coupling into the imaging spectrometer. Thus, the spatial distribution of light from the grating device is only maintained along the longitudinal direction of the slit. By use of the imaging spectrometer (not shown), spectra for each position in the longitudinal direction of the slit may be recorded and analysed e.g. in a computer.

Figure 3:
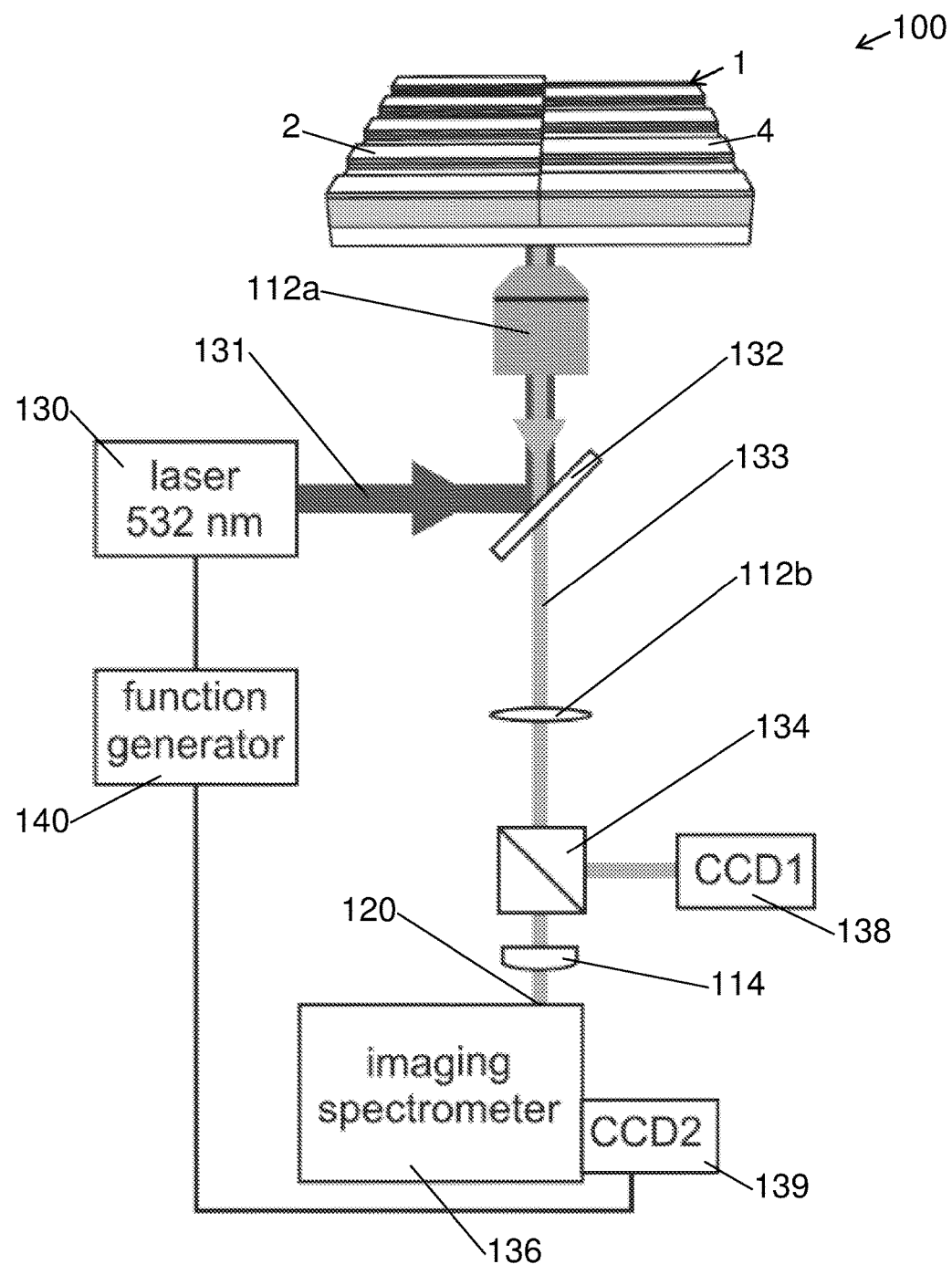
FIG. 3 illustrates an embodiment of the surface refractive index scanning system according to the invention.

FIG. 3 shows an embodiment of the surface refractive index scanning system 100 according to the invention. The embodiment relates to the grating device shown in FIG. 1, and the schematic FIG. 2, wherein like reference numerals refer to identical or similar parts. Therefore, only differences with regards to the two previous figures are described here. This embodiment of the system uses an active grating device, i.e. a grating device comprising a light emitting material. Pump light 131 for exciting the light emitting material is generated in a pump light source, which is here illustrated as a laser 130 for generating 532 nm light. The skilled person will realize that the choice of pumping wavelength depends on the absorption spectrum of the light emitting material used in the grating device. Thus, the use of other pump wavelengths is also foreseen by the inventors. The pump light source may, e.g., also be a flash pump source or other types of non-laser sources. The pump light 131 is coupled via a dichroic mirror 132 onto the grating device 1 to simultaneously pump the first grating region 2 and second grating region 4. To improve coupling of the pump light to the grating device 1, the pump laser light is here shown to be focused by a microscope objective 112a, which is also used to collect and collimate the emitted light 133 generated within the grating device 1. However, in other configurations, the pump light 131 and collected light 133 will have separate optical paths onto and away from the grating device 1. The collimated emitted light 133 is focused onto the entrance slit 120 of the imaging spectrometer 136 by a focusing lens 112b and the cylindrical lens 114. As a convenience, a separate image of the grating device may be formed on an optional CCD array 138 (CCD1), e.g. to inspect the focus of the system. Light for the optional CCD array 138 is split off from the emitted light beam by a beam splitter 134. To use CCD1 to check focus of the system, CCD1 should be arranged in the same distance from the beam splitter 134 as the entrance slit 120. The imaging spectrometer is configured such that the CCD at the spectrograph (CCD2 139) delivers an image where the horizontal direction corresponds to the wavelength of the light. The vertical direction of the image on CCD2 139 corresponds to the longitudinal position along the entrance slit. A function generator 140 is used to generate trigger signals for the pump laser 130 and the imaging spectrometer 136, in particular CCD2 139.

In an example device, the grating device surface emits very narrow laser lines of approx. 0.2 nm full width at half maximum. With the spectrometer used for demonstration by the inventors, the horizontal width of the CCD2 139 will correspond to 55 nm. Thus, several laser lines are well distinguishable on the CCD2 139 image.

The spectrometer CCD signal is analysed and a central emission wavelength is found for each resonance peak/laser line e.g. by using a centre of mass algorithm or fitting a function to the data. The central wavelength of all resonance peaks is monitored and wavelength shifts are calculated with a computer. Wavelength shifts correspond to refractive index changes. An image of the surface refractive index may then be generated by the computer.

According to a demonstration example the optical system is capable of operating with a frame rate of 12 Hz, limited by the read-out time of the spectrometer CCD2 139. By continuously taking images the wavelength shift of each line can be calculated and refractive index changes can be monitored in time and space. In order to demonstrate the functionality of the laser imaging system, the inventors have added a piece of sugar to a microfluidic well with water on top of a grating device, and used the system to monitor how the wavelength of all laser lines was shifting upon the presence of small sugar molecules increasing the refractive index.

Figure 4:
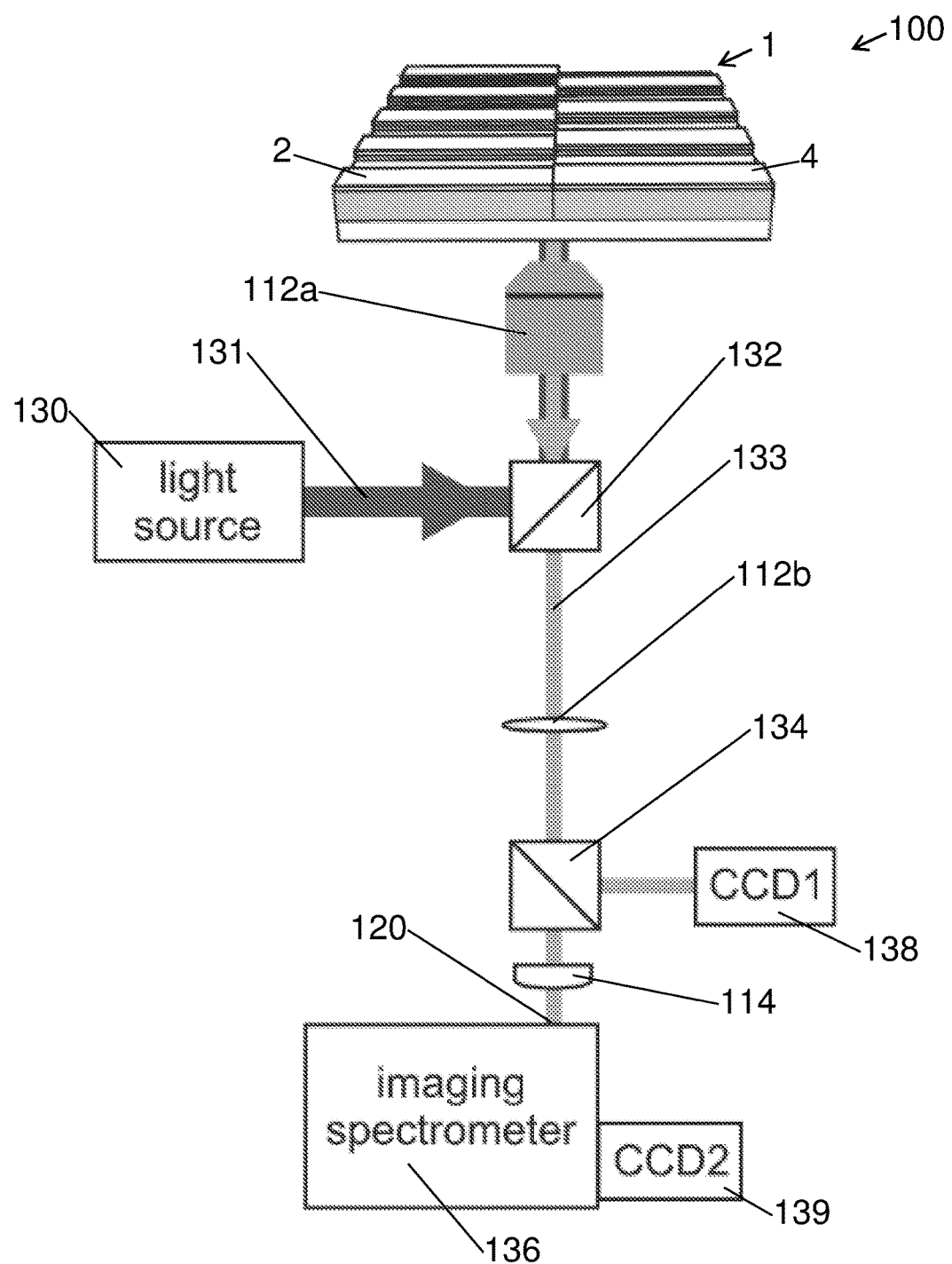
FIG. 4 illustrates an embodiment of the surface refractive index scanning system as arranged in a passive photonic crystal configuration according to the invention.

FIG. 4 shows an alternative embodiment of the surface refractive index scanning system according to the invention, wherein the grating device 1 is a passive device, i.e. not comprising a light emitting material. The embodiment has many similarities with the embodiment shown in FIG. 3 and discussed above. Therefore, only differences between the two embodiments will be discussed here. The grating device 1 is configured to be a guided mode resonance filter. A broadband light source is used for illumination, e.g. a Xenon lamp or an LED. In this case, the resonant wavelengths of the grating regions 2, 4 should be configured to fall within the emission band of the light source. Light reflected from the passive photonic crystal enters into the imaging spectrometer 136 via the cylindrical lens 114 and entrance slit 120, as described above for other embodiments.

Figure 5:
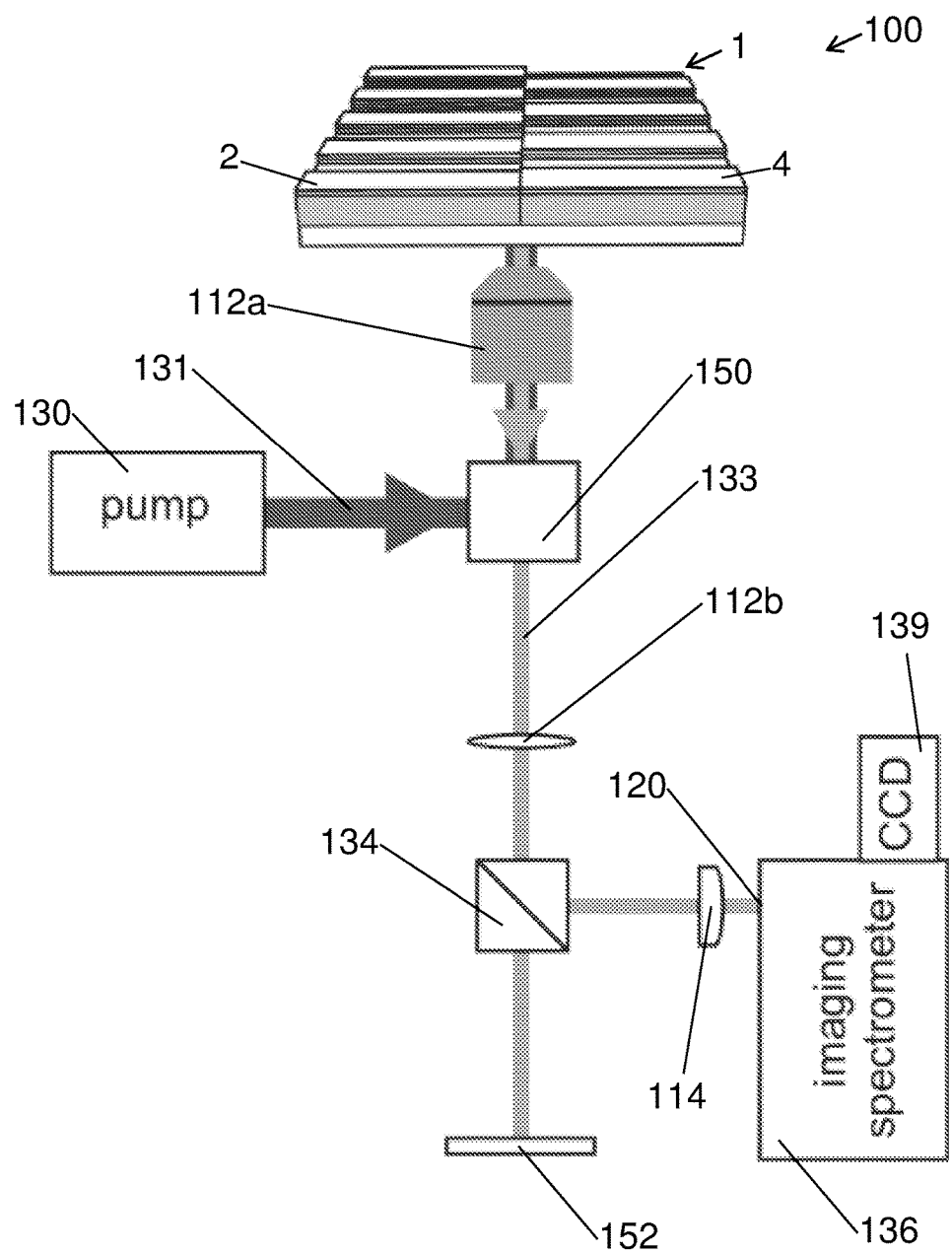
FIG. 5 illustrates an embodiment of the surface refractive index scanning system as arranged in an external cavity laser configuration according to the invention.

FIG. 5 shows an alternative embodiment of the surface refractive index scanning system according to the invention, wherein the grating device 1 is a passive device. The embodiment has many similarities with the embodiment shown in FIG. 3 and discussed above. Therefore, only differences between the two embodiments will be discussed here. The grating device 1 is configured to be a cavity end mirror, the other end of the cavity being formed by mirror 152. Within the cavity, an active element 150 is disposed so as to provide optical gain to light resonant in the cavity. Examples of an active element 150 may be a semiconductor optical amplifier (SOA), a gain crystal, or an organic dye in solution. The active element 150 is here illustrated to be optically pumped by the pump source 130. However, in other embodiments, the active element 150 could alternatively be electrically pumped, depending on the choice of material. In this case the resonant wavelengths of the grating regions 2, 4 should be configured to fall within the amplified spontaneous emission spectrum of the active material. A small fraction of the cavity light is coupled out via a beam splitter 134, and entered into the imaging spectrometer 136 via the cylindrical lens 114 and entrance slit 120, as described above for other embodiments.

Although the present invention has been described in connection with the specified embodiments, it should not be construed as being in any way limited to the presented examples. For instance, the embodiments have shown the use of a cylindrical lens as the optical element for focusing the light from the sample onto the entrance slit of the imaging spectrometer. However, the use of a bended mirror, or another optical element, for this purpose is also envisioned by the inventors and fall within the scope of the invention. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A surface refractive index image acquiring system for characterization of a sample comprising:
    a grating device configured to receive the sample, the grating device comprising at least a first grating region having a first grating width along a transverse direction, and a second grating region having a second grating width in the transverse direction, the first grating region and the second grating region being adjacent in the transverse direction, wherein the first grating region has a grating period $\Lambda_1$ in a longitudinal direction, the longitudinal direction being orthogonal to the transverse direction, and the second grating region has a grating period $\Lambda_2$ in the longitudinal direction, a grating period spacing $\Delta\Lambda = \Lambda_1 - \Lambda_2$ being finite, the first and second grating periods are selected to configure the first and second granting regions to provide optical resonances for light respectively in a first wavelength band and a second wavelength band, light is being emitted, transmitted, or reflected in an out-of-plane direction, wherein the first wavelength band and the second wavelength band are at least partially non-overlapping in wavelength,
    a light source configured to illuminate at least a part of the first grating region and a part of the second grating region simultaneously with light at an illumination wavelength band,
    an imaging system configured to image the emitted, transmitted or reflected light from the grating device, the imaging system comprising an optical element, configured for focusing light in a first transverse direction and for being invariant in an orthogonal transverse direction, the optical element being oriented such that the longitudinal direction of the grating device is oriented to coincide with an invariant direction of the optical element, and an imaging spectrometer comprising an entrance slit having a longitudinal direction oriented to coincide with the invariant direction of the optical element, the imaging spectrometer further comprising a 2-dimensional image sensor.

2. The surface refractive index image acquiring system according to claim 1, wherein the optical element is a cylindrical lens.

3. The surface refractive index image acquiring system according to claim 1, wherein the optical element is a bended mirror.

4. The surface refractive index image acquiring system according to claim 1, wherein the grating device comprises multiple structured regions, including the first grating region and the second grating region, and comprising a number of structured regions in the range 2-100, wherein each of the grating regions are arranged to provide optical resonances for light respectively in corresponding wavelength bands, light is being emitted, transmitted, or reflected in an out-of-plane direction, the corresponding wavelength bands being at least partially non-overlapping.

5. The surface refractive index image acquiring system according to claim 4, wherein the first structured region and/or the second structured region are configured as a second order distributed Bragg reflector, DBR, for providing the optical resonance.

6. The surface refractive index image acquiring system according to claim 4, wherein the grating device comprises a light-emitting material having an emission spectrum, wherein first structured region and the second structured region are configured such that the first wavelength range and the second wavelength range at least partially fall within the emission spectrum of the light-emitting material.

7. The surface refractive index image acquiring system according to claim 6, wherein the grating period spacing $\Delta\Lambda$ between two adjacent grating regions is in the range 0.05 nm-10 nm.

8. The surface refractive index image acquiring system according to claim 6, wherein the light-emitting material is or comprises a dye-doped material.

9. The surface refractive index image acquiring system according to claim 8, wherein the dye-doped material comprises a polymer.

10. The surface refractive index image acquiring system according to claim 1 where the grating device is a passive structure for reflecting or transmitting light in the wavelength ranges.

11. The surface refractive index image acquiring system according to claim 10, wherein the grating period spacing $\Delta\Lambda$ between two adjacent grating regions is in the range 0.5 nm-500 nm.

12. The surface refractive index image acquiring system according to claim 10, wherein the system further comprises an optical gain material and a first cavity end reflector, and wherein the grating device is arranged as a second cavity end reflector, the gain material being disposed between the first cavity end reflector and the second cavity end reflector in an external cavity laser configuration.

13. The surface refractive index image acquiring system according to claim 1, wherein the system is or comprises a microscope system.

14. A method of acquiring a surface refractive index image of a sample, the method comprising:
    providing a grating device configured to receive the sample, the grating device comprising at least a first grating region having a first grating width along a transverse direction, and a second grating region having a second grating width in the transverse direction, the first grating region and the second grating region being adjacent in the transverse direction, wherein the first grating region has a grating period $\Lambda_1$ in a longitudinal direction, the longitudinal direction being orthogonal to the transverse direction, and the second grating region has a grating period $\Lambda_2$ in the longitudinal direction, a grating period spacing $\Delta\Lambda = \Lambda_1 - \Lambda_2$ being finite, wherein the first and second grating periods are selected to configure the first and second grating regions to provide optical resonances for light respectively in a first wavelength band and a second wavelength band, light is being emitted, transmitted, or reflected in an out-of-plane direction, wherein the first wavelength band and the second wavelength band are at least partially non-overlapping in wavelength,
    positioning the sample to be characterized onto the grating device so as to come into contact with the first and/or the second grating region, illuminating at least a part of the first grating region and a part of the second grating region simultaneously with light at an illumination wavelength band, imaging the emitted, transmitted or reflected light from the grating device with an imaging system into a 2-dimensional raw image, the imaging system comprising an optical element, configured for focusing light in a first transverse direction and for being invariant in an orthogonal transverse direction, the optical element being oriented such that the longitudinal direction of the grating device is oriented to coincide with an invariant direction of the optical element, and an imaging spectrometer comprising an entrance slit having a longitudinal direction oriented to coincide with the invariant direction of the optical element, the imaging spectrometer further comprising a 2-dimensional image sensor, oriented along the longitudinal direction of the entrance slit, processing the 2-dimensional raw image to obtain a 2-dimensional map of refractive index change of the sample at the grating regions, by utilizing that each row of pixels in the raw image perpendicular to the longitudinal direction of the entrance slit contains spectrally resolved resonance peaks for each grating region, each resonance peak corresponding to a position along the transverse direction of the grating device, and positions in the raw image along the longitudinal direction translates directly to positions along the longitudinal direction of the grating device.

15. The method according to claim 14 wherein the step of processing the image comprises tracking changes in spectral positions of the resonance peaks to provide a time-resolved image of refractive index changes in the sample.

16. The method according to claim 14, wherein processing the 2-dimensional raw image comprises:

for each row of pixels perpendicular to the longitudinal direction of the entrance slit, detect peak positions in pixels for resonance peaks in the row associated with each grating region, convert each peak position in pixels to a peak wavelength value of resonance, calculate a wavelength shift for each of the peak wavelength values of resonance with regards to reference peak values corresponding to the grating device without the sample present, and calculate refractive index values from the wavelength shifts.

17. The method according to claim 16, wherein finding the peak position in pixels for each of the grating region comprises:

finding a peak pixel as a pixel with a highest intensity reading within a range of pixels associated with that grating region, calculate the peak position in pixels from a range of pixels around the peak pixel using a numerical method.

18. The method according to claim 17, wherein the numerical method is a center of mass calculation or a Lorentzian fit.

* * * * *